(12) United States Patent
Josse et al.

(10) Patent No.: US 12,082,855 B2
(45) Date of Patent: Sep. 10, 2024

(54) SURGICAL SYSTEM AND METHOD

(71) Applicant: Warsaw Orthopedic, Inc., Warsaw, IN (US)

(72) Inventors: Loic Josse, Memphis, TN (US); Bertrand Peultier, Les Hopitaux Neufs (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 363 days.

(21) Appl. No.: 17/605,879

(22) PCT Filed: Apr. 23, 2019

(86) PCT No.: PCT/US2019/028619
§ 371 (c)(1),
(2) Date: Oct. 22, 2021

(87) PCT Pub. No.: WO2020/219017
PCT Pub. Date: Oct. 29, 2020

(65) Prior Publication Data
US 2022/0218395 A1    Jul. 14, 2022

(51) Int. Cl.
*A61B 17/70* (2006.01)
*A61B 17/02* (2006.01)

(52) U.S. Cl.
CPC ........ *A61B 17/7077* (2013.01); *A61B 17/025* (2013.01); *A61B 2017/0256* (2013.01)

(58) Field of Classification Search
CPC .............. A61B 17/7077; A61B 17/025; A61B 2017/0256
USPC ............................ 606/53–59, 250–279, 86 A
See application file for complete search history.

(56) References Cited

U.S. PATENT DOCUMENTS

| | | |
|---|---|---|
| 8,974,497 B2 | 3/2015 | Cho et al. |
| 2008/0154280 A1 | 6/2008 | Schumacher et al. |
| 2012/0290011 A1* | 11/2012 | Justis ................. A61B 17/7076 606/86 A |
| 2015/0164569 A1* | 6/2015 | Reitblat ................. A61B 90/30 606/279 |

(Continued)

FOREIGN PATENT DOCUMENTS

| | | |
|---|---|---|
| KR | 10-1446620 B1 | 10/2014 |
| WO | 2018150214 A1 | 8/2018 |
| WO | 2018150215 A1 | 8/2018 |

OTHER PUBLICATIONS

European Patent Office, 80298 Munich, Germany, Application No. 19926121, Extended European Search Report, Nov. 3, 2022.

(Continued)

*Primary Examiner* — Eduardo C Robert
*Assistant Examiner* — Tara Rose E Carter
(74) *Attorney, Agent, or Firm* — Sorell, Lenna & Schmidt, LLP

(57) ABSTRACT

A surgical system includes an implant support engageable with a receiver of a fastener having a shaft fixed with vertebral tissue. A sleeve having a first mating surface releasably engageable with the implant support and a second mating surface releasably engageable with the receiver. An adaptor connected with the implant support to releasably engage a surgical instrument to distract and/or compress the vertebral tissue. Surgical instruments, constructs, implants and methods are disclosed.

20 Claims, 11 Drawing Sheets

(56) References Cited

U.S. PATENT DOCUMENTS

2018/0036017 A1  2/2018  Donner et al.
2018/0214189 A1  8/2018  Olea et al.
2018/0344481 A1  12/2018  Garcia-Bengochea

OTHER PUBLICATIONS

International Search Report for PCT/US2019/028619 date of completion is Feb. 21, 2020 (3 pages).
China Office Action: China National Intellectual Property Administration: Search Report: Application/Patent No. 201980095626.6: Jan. 26, 2024.

* cited by examiner

SURGICAL SYSTEM AND METHOD

CROSS-REFERENCE TO RELATED APPLICATIONS

This application is a National Stage Application of PCT/US2019/028619 filed Apr. 23, 2019, the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical system is provided. The surgical system includes an implant support engageable with a receiver of a fastener having a shaft fixed with vertebral tissue. A sleeve having a first mating surface releasably engageable with the implant support and a second mating surface releasably engageable with the receiver. An adaptor connected with the implant support to releasably engage a surgical instrument to distract and/or compress the vertebral tissue. In some embodiments, surgical instruments, constructs, implants and methods are disclosed.

In one embodiment, the surgical system includes at least one implant support having a first implant support extending between a proximal end and a distal end. The distal end is configured to capture a first wall of a receiver of a fastener having a shaft fixed with vertebral tissue. The receiver includes the first wall and a second wall that define an implant cavity. A sleeve includes a proximal flange defining mating grooves being releasably engageable with the proximal end and at least one distal projection being releasably engageable with the second wall. An adaptor extends longitudinally along the first implant support for connection with the distal end to releasably engage a surgical instrument to distract and/or compress the vertebral tissue.

In one embodiment, the surgical system includes a first implant support having an adaptor and being releasably engageable with a first wall of a receiver of a first fastener having a shaft fixed with vertebral tissue. The receiver includes the first wall and a second wall that define an implant cavity. A first sleeve includes a flange being releasably engageable with the first implant support and a distal end being releasably engageable with the second wall. A second implant support includes an adaptor and is releasably engageable with a first wall of a receiver of a second fastener having a shaft fixed with vertebral tissue. The receiver of the second fastener includes the first wall and a second wall that define an implant cavity. A second sleeve includes a flange being releasably engageable with the second implant support and a distal end being releasably engageable with the second wall of the second fastener. A surgical instrument includes a first member and a second member. The adaptor of the first implant support is releasably engageable with the first member and the adaptor of the second implant support is releasably engageable with the second member. The members are relatively movable to distract and/or compress the vertebral tissue.

BRIEF DESCRIPTION OF THE DRAWINGS

The present disclosure will become more readily apparent from the specific description accompanied by the following drawings, in which.

DETAILED DESCRIPTION

Figure 1:
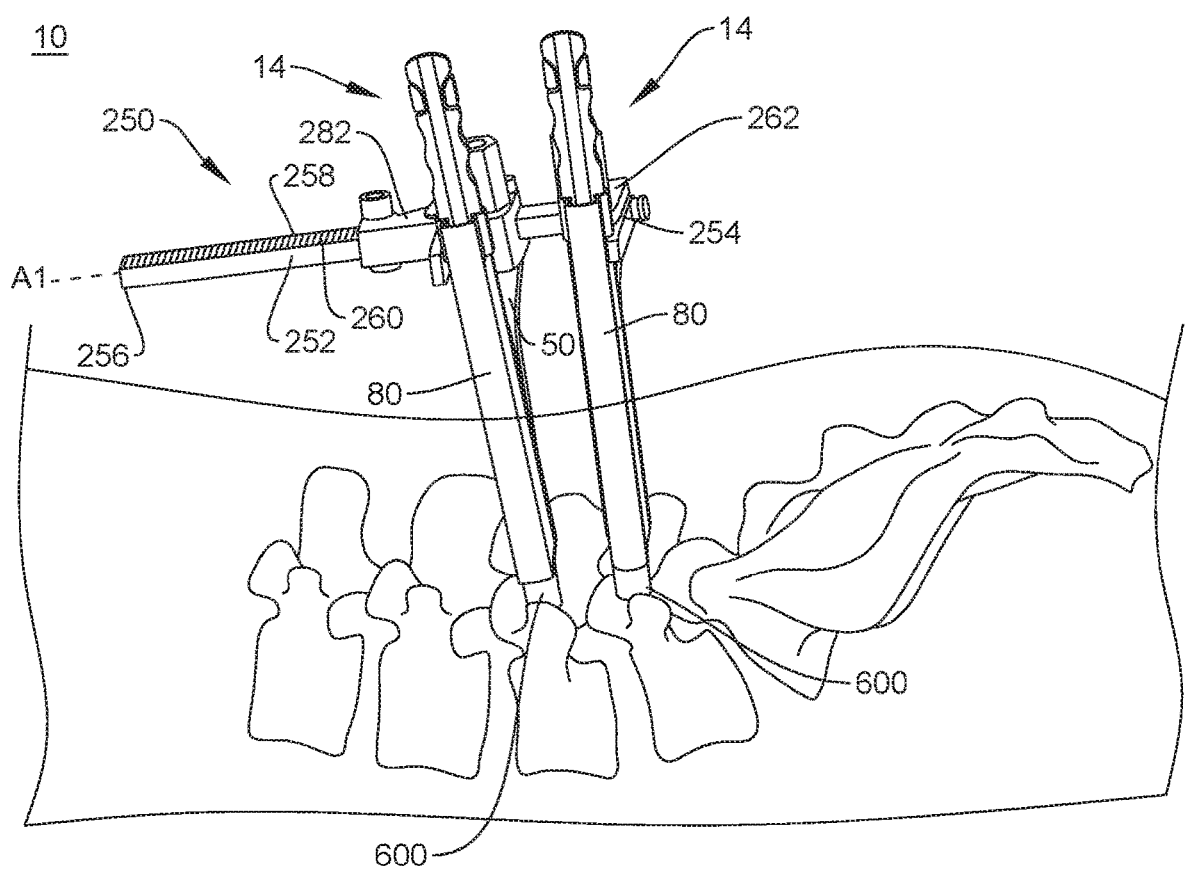
FIG. 1 is a perspective view of components of one embodiment of a surgical system in accordance with the principles of the present disclosure disposed with vertebrae.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal adjusting screw (SAS), a fixed axis screw (FAS) and/or a multi-axial screw (MAS). In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical instrument employed with a surgical method including degenerative lumbar spine fusion. In some embodiments, the present surgical system includes a surgical instrument employed with a surgical method including the step of segmental posterior stabilization with MAS screws. In some embodiments, the present surgical system includes a surgical method including an interbody fusion, posterior lumbar interbody fusion (PLIF), transforaminal lumbar interbody fusion (TLIF) utilizing a minimally invasive surgical approach or a percutaneous approach. In some embodiments, the present surgical system includes bone screw extenders, tissue retractors and a distractor/compressor system. In some embodiments, the present surgical system includes segmental distraction to facilitate decompression, including final construct compression. In some embodiments, the present surgical system includes radio transparent tissue retractor blades.

In some embodiments, the present surgical system includes a surgical instrument employed with a surgical method including the step of: connecting extenders, such as, for example, implant supports with MAS screws; connecting a sleeve with the implant support and the bone screw; and employing a universal screw driver for percutaneous implantation of the bone screw utilizing a PAK needle, guidewire or fluoroscopy. In some embodiments, the present surgical system includes screw based segmental distraction. In some embodiments, the segmental distraction is accomplished by utilizing a distractor, angulation modules and lock elements to distract the bone screw heads.

In some embodiments, the present surgical system includes a dilator configured to evaluate tissue depth from graduations disposed thereon. In some embodiments, the present surgical system includes a retractor having a selection of blade lengths. In some embodiments, the present surgical system includes the step if inserting the retractor blades along the dilator and manipulating and/or adjusting angulation of the blades and the distance between the blades. In some embodiments, the present surgical system includes a light source configured for connection with the retractor.

In some embodiments, the adaptor is employed with a surgical method including the step of inserting the adaptor with a surgical site and the step of sliding a sleeve along the implant support. In some embodiments, the method includes the step of securing the sleeve to the implant support. In some embodiments, the method includes the step of connecting a compressor/distractor with the adaptor. In some embodiments, the method includes the step of connecting an angulation module with the adaptor, the compressor/distractor and the extender. In some embodiments, the method includes the step of securing the angulation module, the compressor/distractor and the adaptor with a locking element. In some embodiments, the method includes the step of distracting and/or compressing a posterior ligament. In some embodiments, the method includes the step of actuating a rack and pinion mechanism disposed with the compressor/distractor to facilitate distraction or compression.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise, Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior."

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure, Alternate embodiments are disclosed. Reference is made to the exemplary embodiments of the present disclosure, which are illustrated in the accompanying figures. Turning to FIGS. 1-6, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a patient body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Surgical system 10 includes an extender, such as, for example, an implant support and a sleeve 80, both engageable with a bone screw 600. Implant support 14 includes an adaptor 50 connectable to a surgical instrument, such as, for example, a compressor/distractor 250 to facilitate manipulation of tissue, as described herein.

Figure 2:
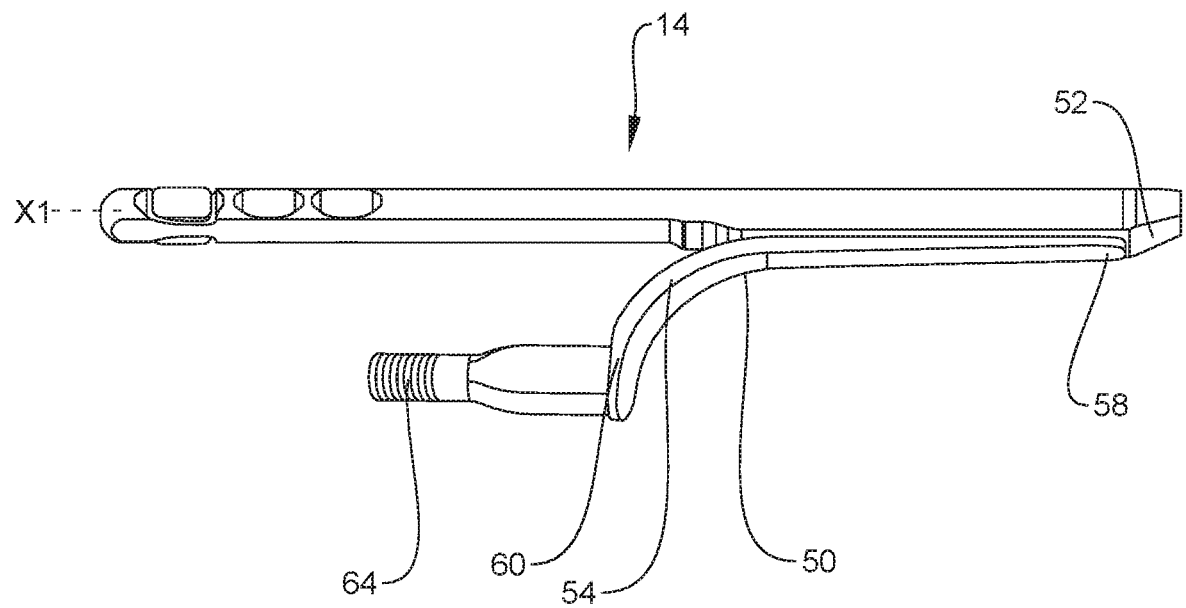
FIG. 2 is a perspective view of components of one embodiment of a surgical system in accordance with the principles of the present disclosure.
Figure 3:
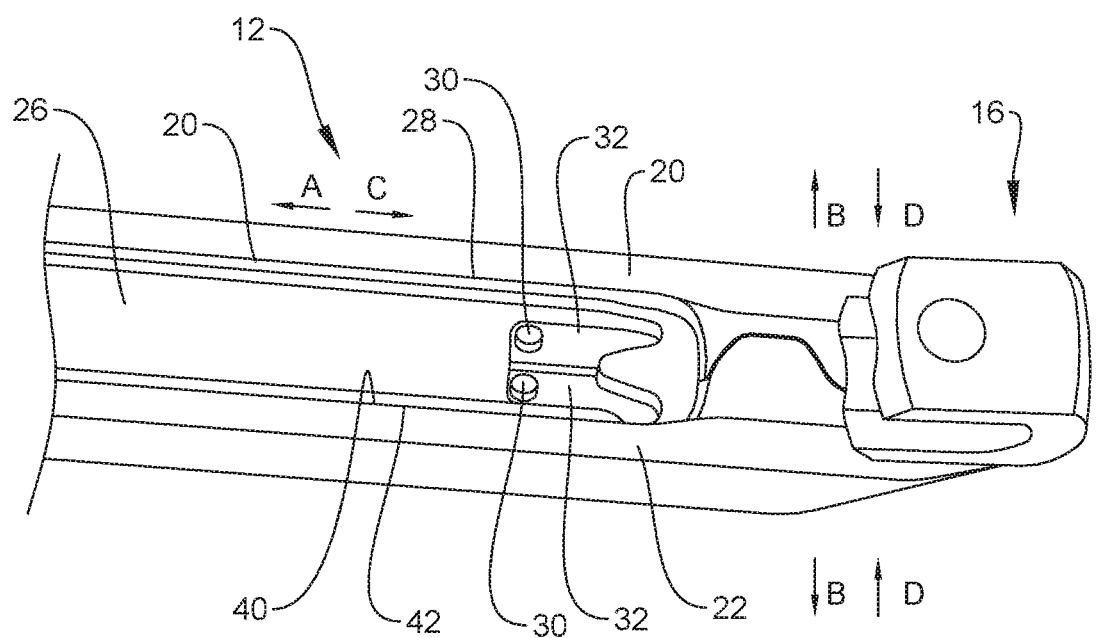
FIG. 3 is a break away perspective view of components of one embodiment of a surgical system in accordance with the principles of the present disclosure.

Implant support 14 extends along an axis X1, as shown in FIG. 2. Implant support 14 includes an extension 20 and an extension 22, as shown in FIG. 3. Extensions 20, 22 are relatively moveable to each other via relative translation of a translation element, such as, for example, a slide 26 disposed with implant support 14, as shown in FIG. 3. Slide 26 is manipulated for translation within channel 28 to move extensions 20, 22 between an open orientation and a closed, capture orientation. Slide 26 is translated, in a direction shown by arrow A in FIG. 3, to cause extensions 20, 22 to rotate and expand, in a direction shown by arrows B, to the open orientation. In the open orientation, pins 30 are seated in a bottom of slots 32 of slide 26. Slide 26 is translated, in a direction shown by arrow C in FIG. 4, to cause extensions 20, 22 to rotate and contract, in a direction shown by arrows D, to the closed orientation to capture a wall 604 of a receiver 602 of bone screw 600, as shown in FIG. 3. In the closed orientation, pins 30 are seated in at the top of slots 32. In some embodiments, extensions 20, 22 are flexible to facilitate contraction.

Positioning of implant support 14 with wall 604 provides for direct access to receiver 602 to facilitate insertion of a spinal rod. In some embodiments, one or more implant supports 14 are manipulable, as described herein, to provide a counter-torque for small deformity maneuvers and manipulation of vertebrae during a surgical treatment, for example, to displace, pull, twist or align vertebrae. Implant support 14 includes a surface 40 that defines a channel 42. Channel 42 is configured for disposal of slide 26, as described herein.

Figure 6:
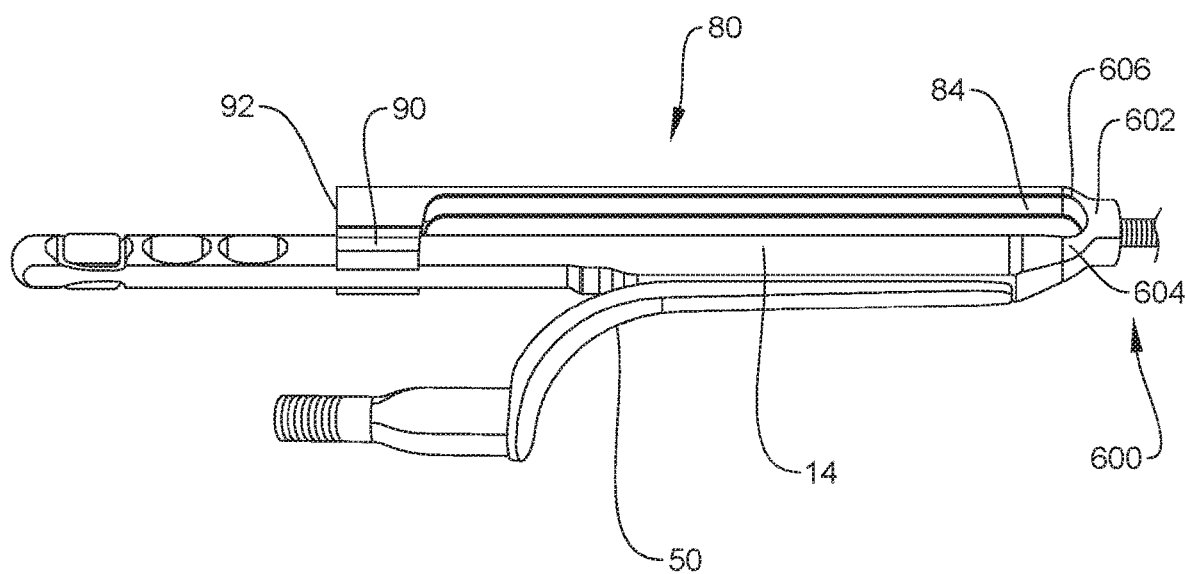
FIG. 6 is a perspective view of the components shown in FIG. 5.

Adaptor 50 is pivotable and/or rotatable relative to implant support 142 and/or bone screw 600, as shown in FIGS. 2 and 6. Rotation of adaptor 50 facilitates engagement of implant support 14 via adaptor 50 with compressor/distractor 250, as described herein. Adaptor 50 extends between an end 54 and an end 56. End 54 is connected to sleeve 52 by a pin hinge 58. Pin 58 facilitates rotation of adaptor 50 relative to implant support 14 and/or bone screw 600. In some embodiments, adaptor 50 may be variously oriented relative to implant support 14, such as, for example, transverse, perpendicular, angular and/or offset. End 56 includes an arm 60 extending therefrom. Rotation of arm 60 facilitates connection of adaptor 50 and implant support 14 with compressor/distractor 250, as described herein. In some embodiments, arm 60 is may be variously oriented relative to axis X1, such as, for example, parallel, perpendicular, angular and/or offset.

Arm 60 includes a surface 62 that defines a threaded lock surface 64. Surface 64 is engageable with a lock nut 274 to fix compressor/distractor 250 with implant supports 14 and adaptors 50, as described herein. In some embodiments, surface 64 may have alternative locking and/or tool engaging surfaces, such as, for example, rectangular, polygonal, hexalobe, oval, irregular, cruciform, phillips, square, polygonal or star cross sectional configuration.

Figure 4:
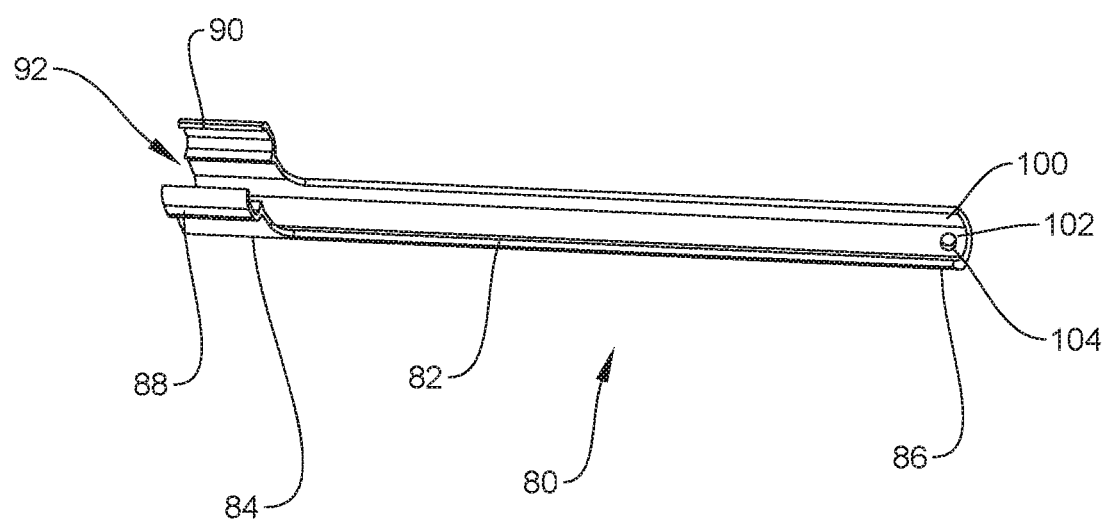
FIG. 4 is a perspective view of components of one embodiment of a surgical system in accordance with the principles of the present disclosure.
Figure 5:
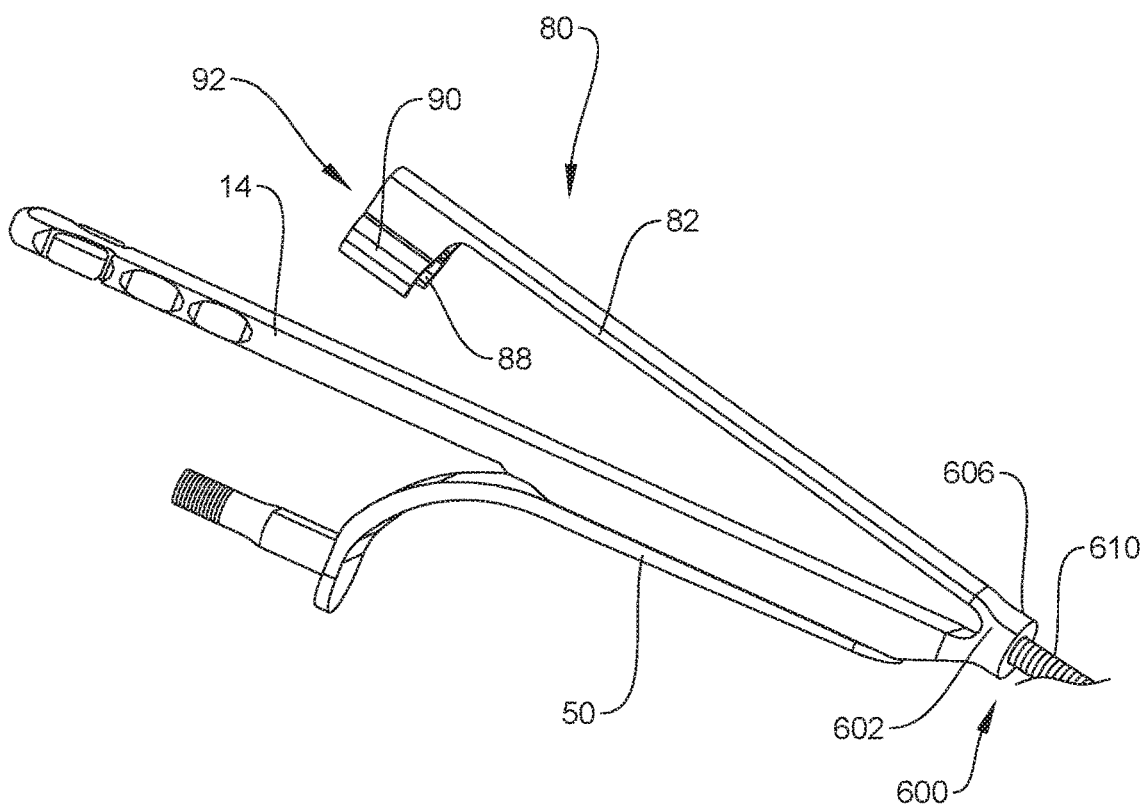
FIG. 5 is a perspective view of components of one embodiment of a surgical system in accordance with the principles of the present disclosure.
Figure 7:
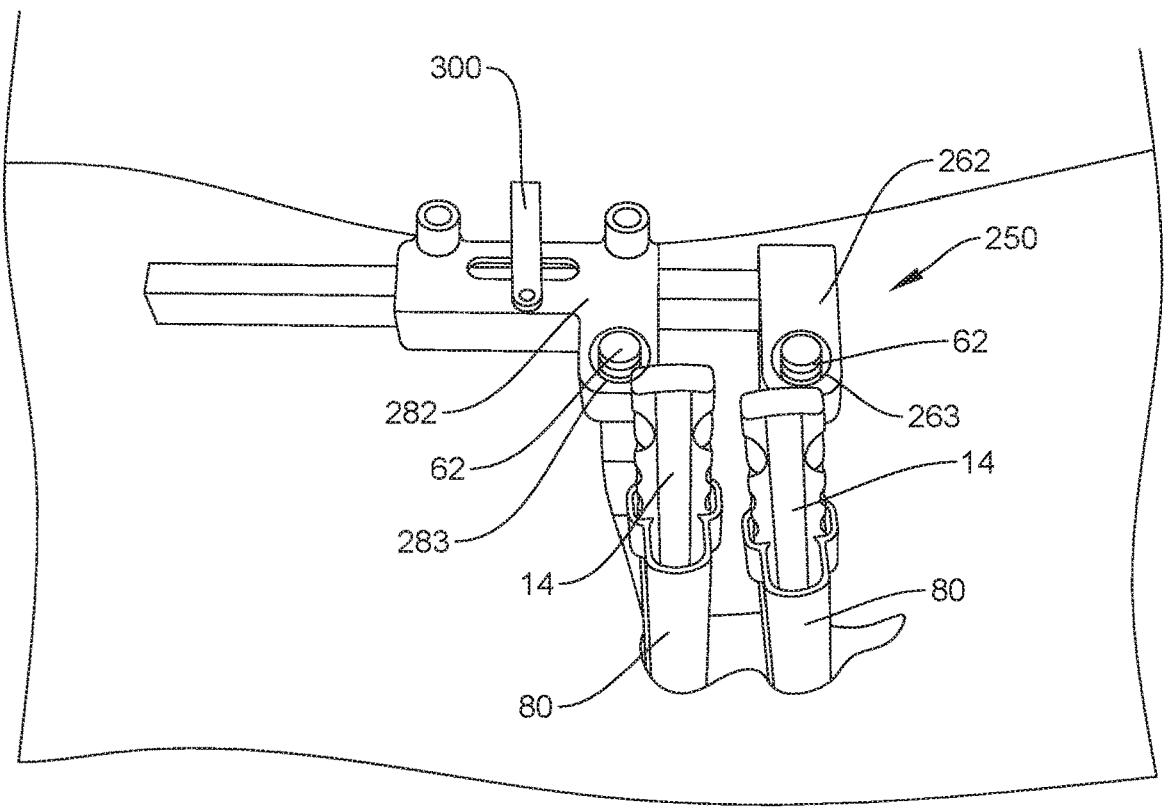
FIG. 7 is a perspective view of components of one embodiment of a surgical system in accordance with the principles of the present disclosure with a patient body.

Sleeve 80 is connectable with implant support 14 and wall 606. Sleeve 80 includes a body 82 extending between an end 84 and an end 86, as shown in FIG. 7. Body 82 extends along implant support 14. End 84 includes a flange 88 and a flange 90 that define a mating surface, such as, for example, mating grooves 92. Mating grooves 92 are configured for disposal of a proximal portion of implant support 14, as shown in FIGS. 4-6. Flanges 88, 90 are flexible such that flanges 88, 90 snap fit into engagement with implant support 14. Upon disposal of implant support 14 with mating grooves 92, sleeve 80 is disposed in a configuration to capture a wall 606 of receiver 602, as shown in FIGS. 5 and 6.

End 86 includes a surface 100 that defines a mating surface 102. Surface 102 is configured for capture of wall 606. Surface 102 includes a distal projection 104 configured for engagement with a cavity 608 disposed with wall 606 of receiver 602 to facilitate engagement.

Bone screw 600 includes, such as, for example, a multi-axial receiver 602 and a shaft 610. Receiver 602 is moveable relative to shaft in a multi axial configuration. Receiver 602 includes spaced apart walls 604, 606, as shown in FIG. 5. Receiver 602 is configured for engagement with implant support 14 and sleeve 80, as described herein. Walls 604, 606 each include a surface that defines cavities 608. Cavities 608 facilitate connection with implant support 14 and/or sleeve 80, as described herein. Walls 604, 606 include an inner surface that defines a U-shaped passageway 612 for disposal of a spinal rod, as described herein. The inner surface of receiver 602 includes a thread form configured for engagement with a set screw.

In assembly, operation and use, surgical system 10, similar to the systems and methods described herein, is employed with a surgical procedure, for treatment of a spine of a patient including vertebrae V, as shown in FIGS. 7-19. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 19:
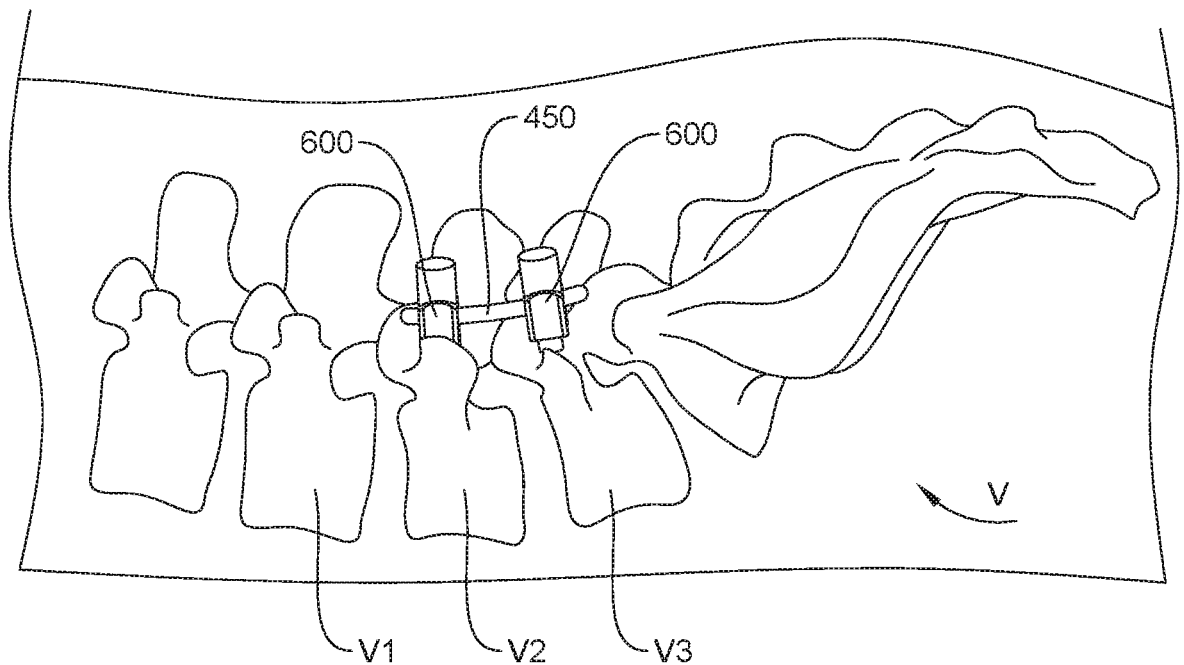
FIG. 19 is a side view of components of one embodiment of a surgical system in accordance with the principles of the present disclosure disposed with vertebrae.

Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 19. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Pilot holes or the like are made in selected vertebrae V1 and V3 for receiving bone screws 600. Implant support 14, including adaptor 50, is engaged with wall 604 of receiver 602, as described herein. Sleeve 80 is engaged with wall 606 of receiver 602, as described herein. Mating grooves 88, 90 are engaged with implant support 14, as described herein. A driver 650 is disposed adjacent vertebrae V at a surgical site and is manipulated to drive, torque, insert or otherwise connect bone screw 600 with vertebrae.

Compressor/distractor 250 is connected with implant supports 14 via adaptors 50, as shown in FIG. 7, to allow for distraction and/or compression of vertebrae V connected with bone screw 600. Compressor/distractor 250 includes a longitudinal element, such as, for example, a rack 252, as shown in FIG. 1. Rack 252 extends between an end 254 and an end 256 defining a longitudinal axis A1 Rack 252 is configured to connect adjacent implant support 14. Rack 252 includes an outer surface 258 having a plurality of teeth, such as, for example, splines 260 engageable with an arm 282, as described herein. Rack 252 includes an arm 262 extending from end 254. In some embodiments, arm 262 is attached with rack 252 with, for example, with clips, hooks, adhesives and/or flanges.

Arm 262 includes a surface that defines an opening 263 configured for disposal of surface 62 for mounting compressor/distractor 250 with implant support 14, adaptor 50 and sleeve 80, as shown in FIG. 7. Rack 252 includes arm 282 that is axially translatable along axis A1 relative to arm 262. Arm 282 includes a surface that defines an opening 283 configured for disposal of surface 62 for mounting compressor/distractor 250 with implant support 14, adaptor 50 and sleeve 80.

Compressor/distractor 250 includes a ratchet, which includes splines 260 and arm 282 engageable in a bi-directional and/or two-way ratchet configuration. Arm 282 includes a latch 300 that includes a pinion or pawl (not shown) engageable with splines 260. Latch 300 is pivotable relative to arm 282 for disposal in a distraction position, as described herein. In the distraction position, latch 300 engages rack 252 to allow axial and/or incremental translation of arm 282 relative to arm 262/rack 252 and prevents axial translation of arm 282 relative to arm 262/rack 252, in an opposing direction. As such, distraction of vertebral tissue connected with implant supports 14 can be performed.

Latch 300 is pivotable relative to arm 282, as shown in FIG. 7. For example, latch 300 is pivotable for disposal in a neutral position. In the neutral position, latch 300 disengages from rack 252 to allow free axial translation of arm 262/rack 252 relative to arm 282. Latch 300 is pivotable relative to arm 282 for disposal in a compression position (not shown). In the compression position, latch 300 engages rack 252 to allow axial and/or incremental translation of arm 282 relative to arm 262/rack 252 to compress vertebral tissue and prevents axial translation of arm 282 relative to arm 262/rack 252, in an opposing direction. As such, compression of vertebral tissue connected with implant supports 14 can be performed. In some embodiments, a rotatable key 302 includes a gear surface engageable with splines 260 to axially and/or incrementally translate rack 252 to facilitate distraction and/or compression, as described herein.

Figure 8:
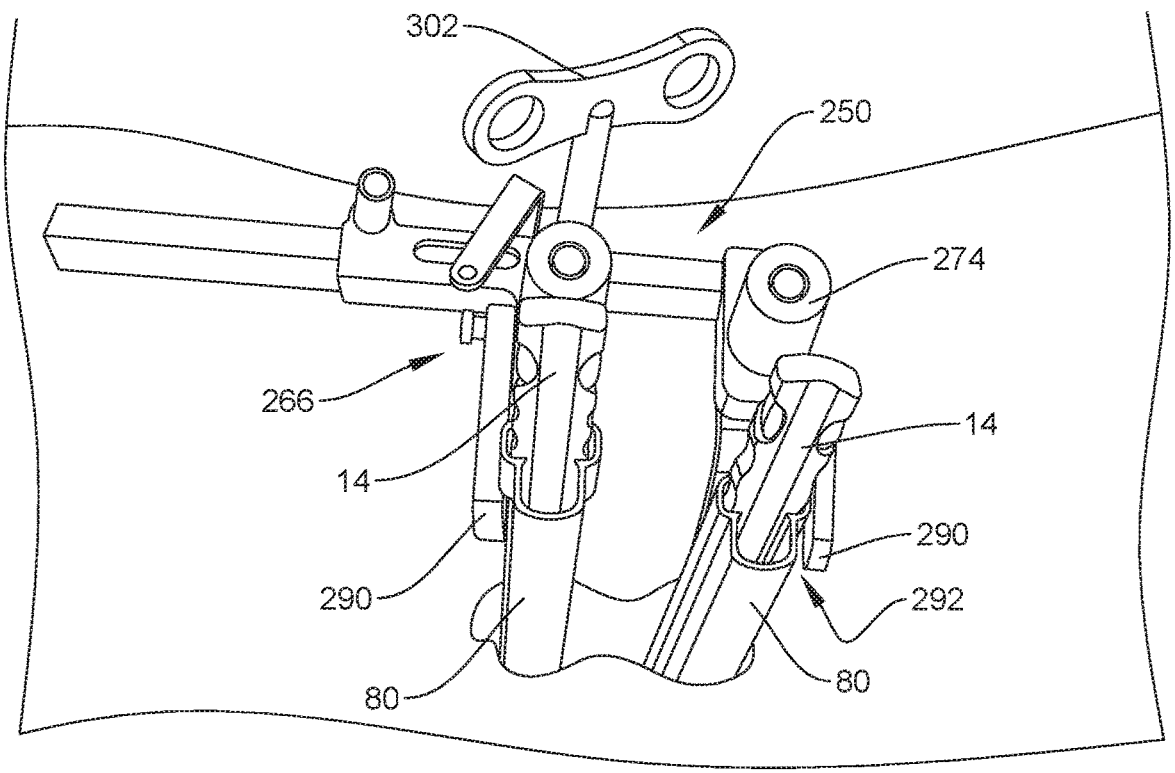
FIG. 8 is a perspective view of components of one embodiment of a surgical system in accordance with the principles of the present disclosure with a patient body.
Figure 9:
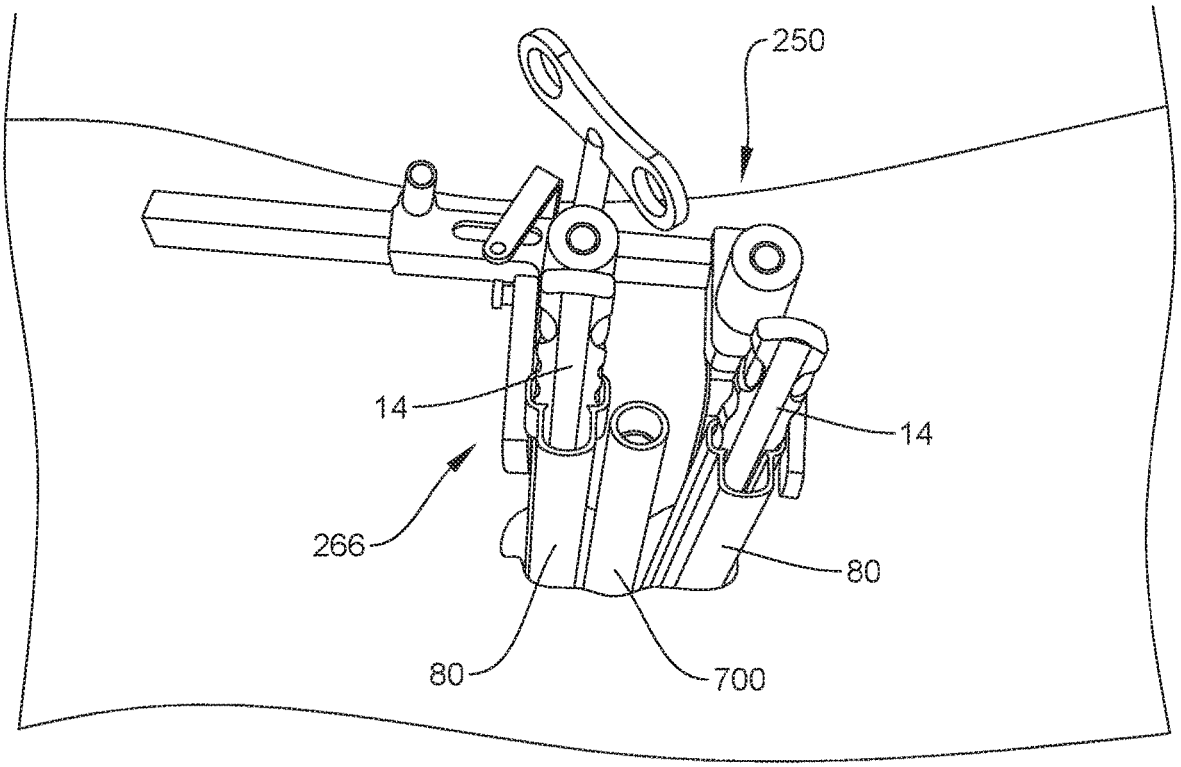
FIG. 9 is a perspective view of components of one embodiment of a surgical system in accordance with the principles of the present disclosure disposed with a patient body.

Angulation module 266 is connectable with compressor/distractor 250, implant supports 14 and adaptor 50, as shown in FIGS. 8 and 9. Module 266 is mounted with surfaces 62 for connection with compressor/distractor 250, implant supports 14 and adaptor 50 via lock nut 274. Module 266 includes spaced apart arms 290 that define a cavity 292. Arms 290 are configured for capture of implant supports 14 to facilitate parallel distraction. Module 266 is fixed with implant supports 14 to allow for angulation and/or correction of vertebral tissue connected with implant supports 14, individually, in combination or simultaneously. In some embodiments, engagement of implant supports 14 with module 266 facilitates parallel manipulation of vertebrae attached with implant supports 14. In some embodiments, modules 266 are connected with compressor/distractor 250 and/or implant supports 14 to maintain a corrected vertebral angle of vertebrae during distraction and/or compression, as described herein.

Figure 10:
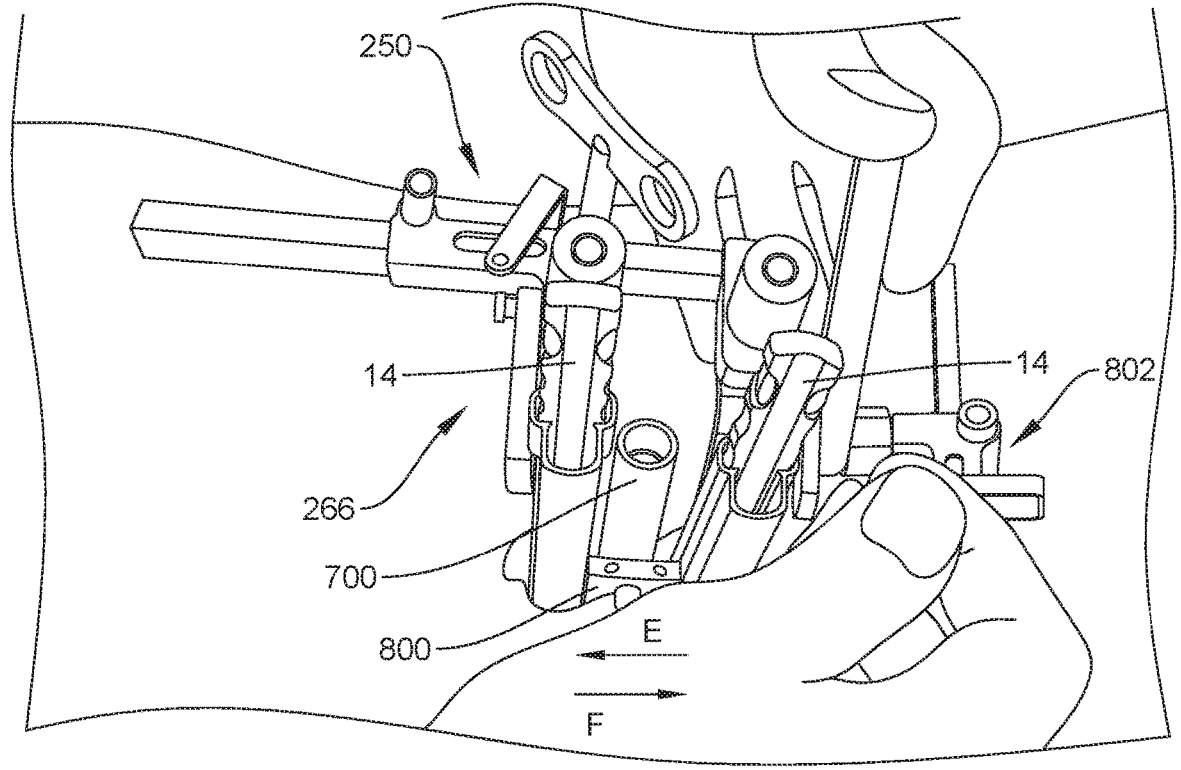
FIG. 10 is a perspective view of components of one embodiment of a surgical system in accordance with the principles of the present disclosure being handled by a user with vertebrae.

For example, latch 300 is pivotable to the distraction position, as described herein, to allow translation of arm 282, in the direction shown by arrow E, and prevent translation of arm 282, in the direction shown by arrow F, relative to arm 262/rack 252, as shown in FIG. 10. As such, distraction of vertebrae V1, V3 connected with implant supports 14 can be performed.

Figure 11:
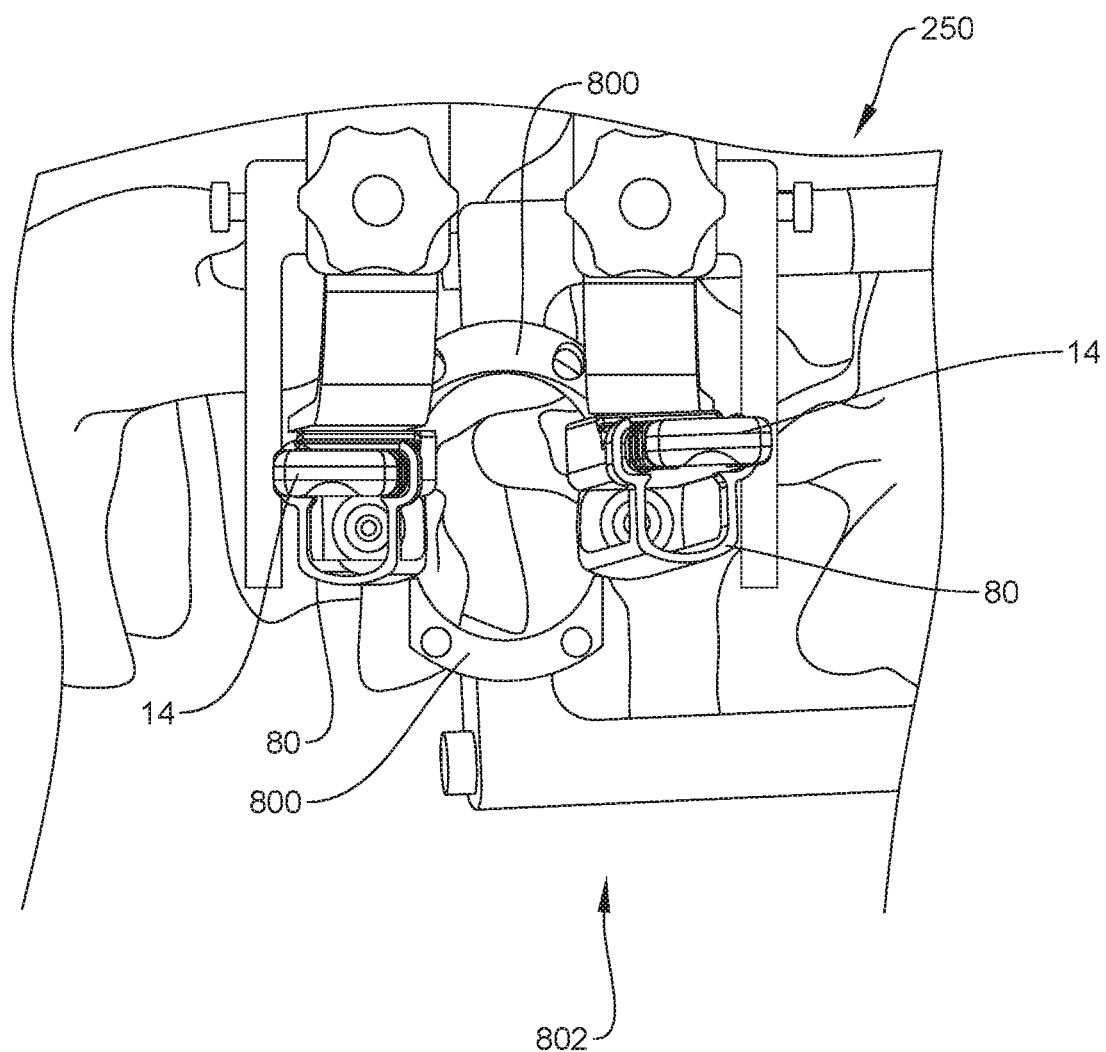
FIG. 11 is a top view of components of one embodiment of a surgical system, in accordance with the principles of the present disclosure with vertebrae.
Figure 12:
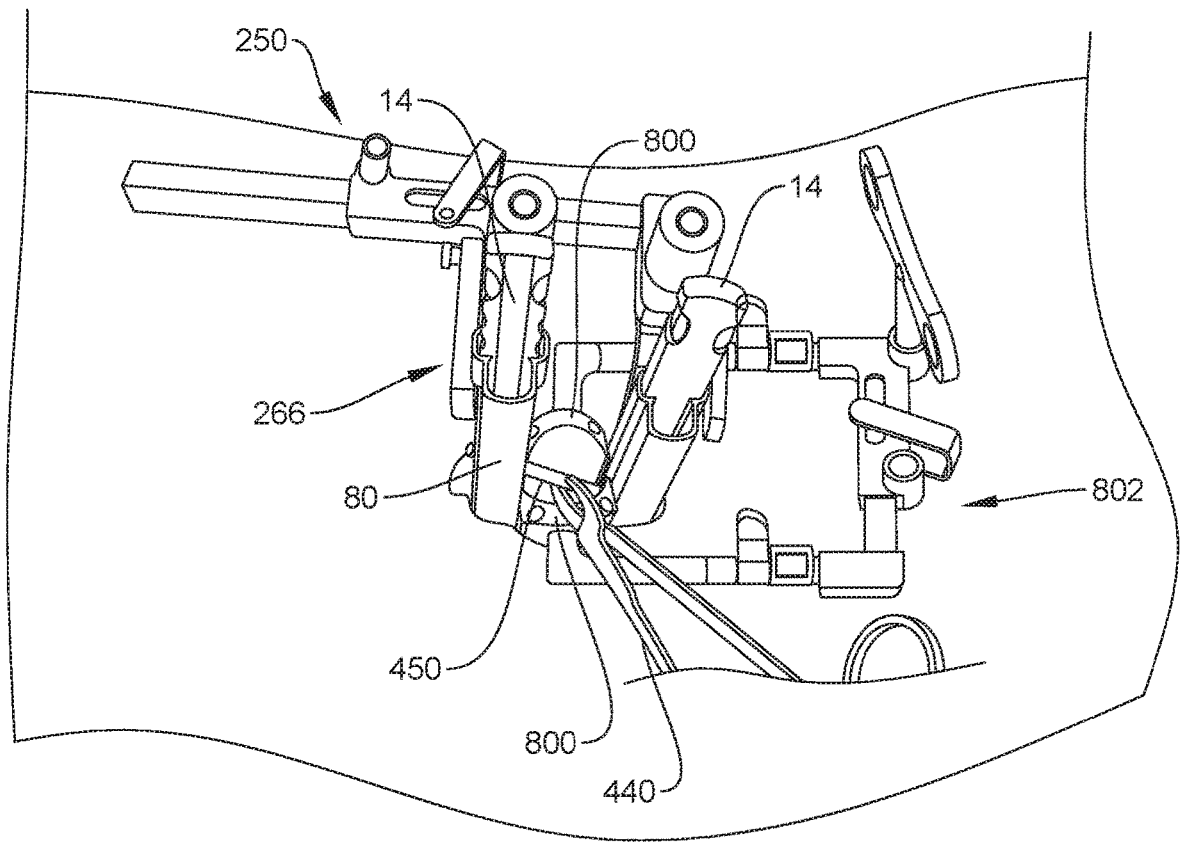
FIG. 12 is a perspective view of components of one embodiment of a surgical system in accordance with the principles of the present disclosure disposed with a patient body.

In some embodiments, a dilator 700 is inserted between implant supports 14 into contact with bony anatomy and determine tissue depth. In some embodiments, a retractor blades 800 are translated along dilator 700 into engagement with the bony anatomy, as shown in FIG. 10. Blades 800 are disposed with tissue to form a surgical passageway, as shown in FIG. 11, to facilitate insertion of a spinal implant, such as, for example, an interbody spinal implant. In some embodiments, blades 800 are selected according to a desired length and/or width. A blade holder 802 is attached to blades 800 and utilized to manipulate and/or adjust blades 800, as shown in FIG. 10.

In some embodiments, a light source is disposed with retractor 800 to provide illumination to the working channel. In some embodiments, compressor/distractor 250 is employed segmental distraction to facilitate insertion of an interbody implant and decompressing tissue.

Figure 13:
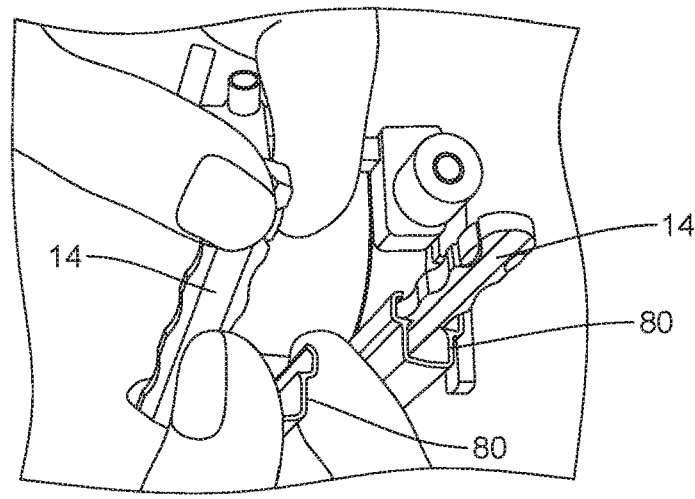
FIG. 13 is a perspective view of components of one embodiment of a surgical system in accordance with the principles of the present disclosure being handled by a user disposed with a patient body.
Figure 14:
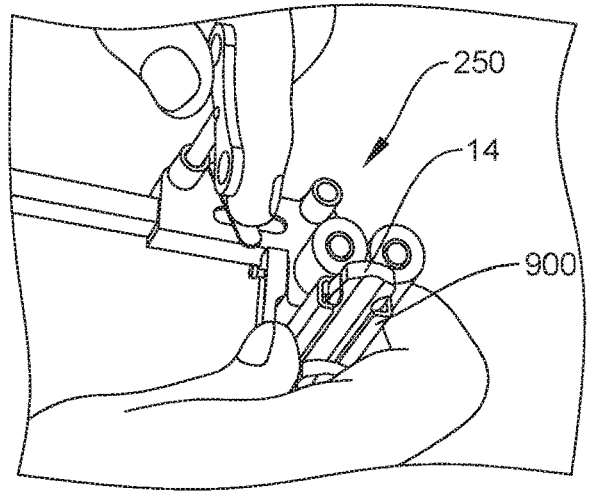
FIG. 14 is a perspective view of components of one embodiment of a surgical system in accordance with the principles of the present disclosure being handled by a user disposed with a patient body.
Figure 15:
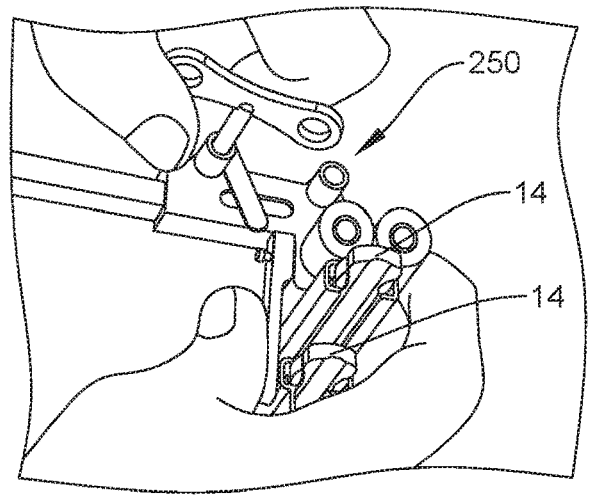
FIG. 15 is a perspective view of components of one embodiment of a surgical system in accordance with the principles of the present disclosure being handled by a user with a patient body.
Figure 16:
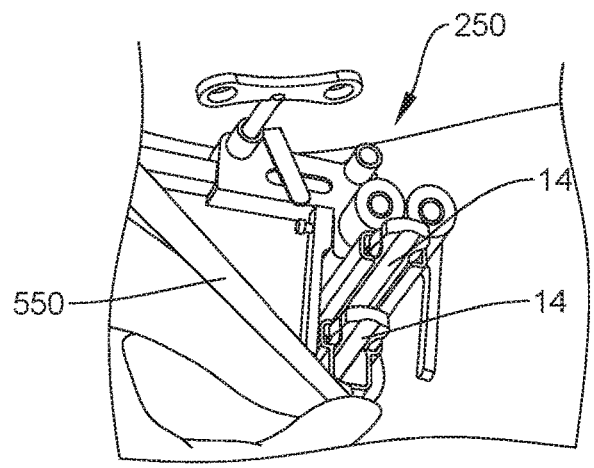
FIG. 16 is a perspective view of components of one embodiment of a surgical system in accordance with the principles of the present disclosure being handled by a user with a patient body.

In some embodiments, a rod inserter 440 is engaged with a spinal rod 450 to direct and/or guide spinal rod 450 through implant supports 14 into receiver 602. In some embodiments, a driver (not shown) is utilized to engage a set screw (not shown) with bone screws 600 to fix one end of spinal rod 450. Retractor 800 is removed, and blades are translated out of the surgical site, as shown in FIG. 13. One of sleeves 80 is disengaged from implant supports 14, as shown in FIG. 13, and implant supports 14 are crossed. In some embodiments, a crossing block 900 captures the crossed implant supports 14, as shown in FIG. 14. Compressor/distractor 250 is disposed in a compression position, as described herein, and key 302 is rotated to selectively compress vertebrae V. The driver 550 is utilized to engage a second set screw (not shown) with bone screw 600 to fix a second end of spinal rod 450, as shown in FIG. 16.

Figure 17:
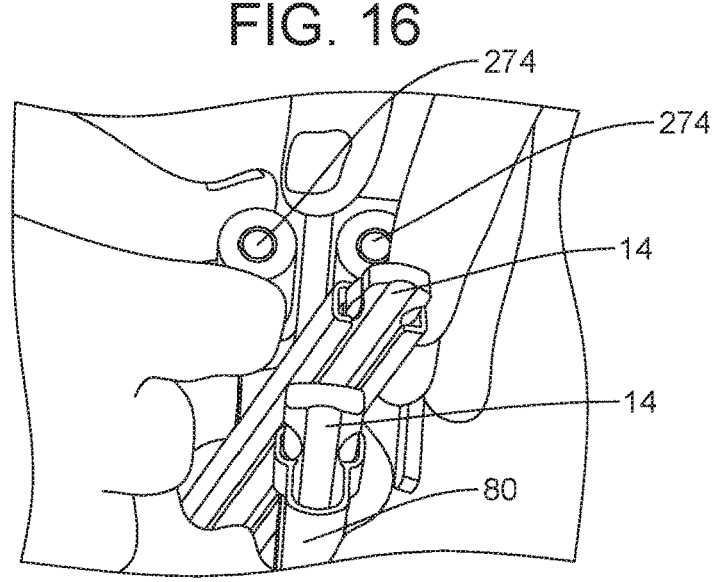
FIG. 17 is a perspective view of components of one embodiment of a surgical system in accordance with the principles of the present disclosure being handled by a user with a patient body.
Figure 18:
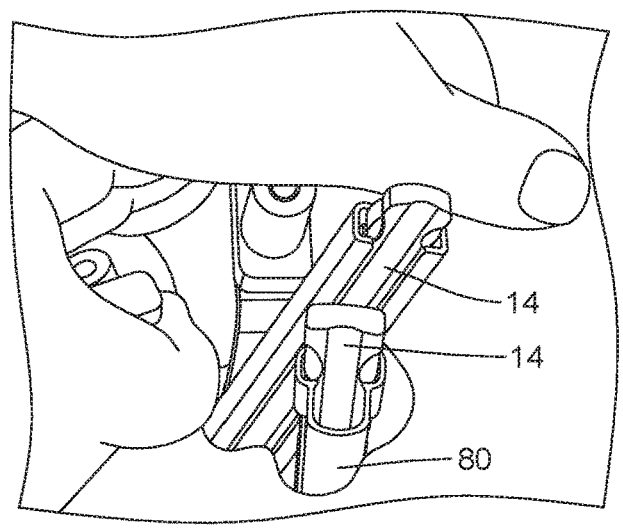
FIG. 18 is a perspective view of components of one embodiment of a surgical system in accordance with the principles of the present disclosure being handled by a user with a patient body.

Compressor/distractor 250 and implant supports 14 are removed, as shown in FIGS. 17-18. For example, lock nuts 274 are disengaged from surface 64. Latch 300 is set to the neutral position. Angulation modules 266 and compressor/distractor 250 are disengaged from adaptors 50 and implant supports 14. Implant supports 14 are removed.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or a plurality of alternate surgical instruments, each configured for mating engagement in a quick release configuration with spinal constructs, as described herein. This configuration facilitates the interchangeability of the spinal constructs with the alternate surgical instruments. In some embodiments, surgical system 10 includes one or a plurality of alternate surgical instruments, such as, for example, inserters, extenders, reducers, spreaders, distracters, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
   a fastener comprising a receiver and a shaft that is configured to be fixed with vertebral tissue, the receiver comprising spaced apart first and second arms;
   an implant support coupled to the first arm;
   a sleeve having a first mating surface defining a cavity having the implant support positioned therein to releasably engage the sleeve with the implant support, the sleeve having a second mating surface releasably engaged with the second arm; and
   an adaptor connected with the implant support to releasably engage a surgical instrument to distract and/or compress the vertebral tissue.

2. A surgical system as recited in claim 1, wherein the arms define an implant cavity therebetween.

3. A surgical system as recited in claim 1, wherein the sleeve includes spaced apart flexible flanges that define the cavity.

4. A surgical system as recited in claim 1, wherein the first mating surface includes a flange engageable with the first implant support.

5. A surgical system as recited in claim 4, wherein the first mating surface includes spaced apart first and second flanges, the flanges being flexible such that the flanges snap fit into engagement with the implant support.

6. A surgical system as recited in claim 1, wherein the first mating surface includes a proximal flange engageable with a proximal portion of the implant support and the second mating surface includes at least one distal projection engageable with the second arm, the proximal flange defining the cavity.

7. A surgical system as recited in claim 1, wherein the adaptor is rotatable relative to the first implant support.

8. A surgical system as recited in claim 1, wherein the adaptor is connected with the implant support by a hinge such that the adaptor is rotatable relative to the implant support about the hinge.

9. A surgical system as recited in claim 8, wherein the hinge is a pin hinge.

10. A surgical system as recited in claim 1, wherein the surgical instrument includes a first member and a second member, the members being relatively movable to distract and/or compress the vertebral tissue.

11. A surgical system as recited in claim 10, wherein the surgical instrument includes a compressor/distractor having a ratchet that prevents movement of the second member relative to the first member in a first direction and a second direction.

12. A surgical system as recited in claim 1, wherein the surgical instrument includes at least one stop engageable with the implant support to resist and/or prevent rotation of the implant support.

13. A surgical system comprising:
    a fastener comprising a receiver and a shaft that is configured to be fixed with vertebral tissue, the receiver comprising spaced apart first and second arms that define an implant cavity therebetween;
    an implant support extending between a proximal end and a distal end, the distal end being coupled to the first arm;
    a sleeve including a proximal flange defining mating grooves being releasably engaged with the proximal end and at least one distal projection being releasably engageable with the second arm; and
    an adaptor extending longitudinally along the first implant support for connection with the distal end to releasably engage a surgical instrument to distract and/or compress the vertebral tissue.

14. A surgical system as recited in claim 13, wherein the adaptor is rotatable relative to the first implant support.

15. A surgical system as recited in claim 13, wherein the adaptor is connected with the implant support by a pin hinge such that the adaptor is rotatable relative to the implant support about the pin hinge.

16. A surgical system comprising:
    a first fastener comprising a first receiver and a first shaft that is configured to be fixed with vertebral tissue, the first receiver comprising spaced apart first and second arms that define a first implant cavity therebetween;
    a first implant support coupled to the first arm;
    a first adaptor connected with the first implant support;
    a first sleeve including a flange defining a cavity having the first implant support positioned therein, the first sleeve comprising a distal end that is releasably engageable with the second arm;
    a second fastener comprising a second receiver and a second shaft that is configured to be fixed with the vertebral tissue, the second receiver comprising spaced apart first and second arms that define a second implant cavity therebetween;
    a second implant support coupled to the first arm of the second fastener;
    a second adaptor connected with the second implant support;
    a second sleeve including a flange defining a cavity having the second implant support positioned therein, the second sleeve comprising a distal end being that is releasably engageable with the second arm of the second fastener; and
    a surgical instrument including a first member and a second member,
    the first adaptor being releasably engageable with the first member and the second adaptor being releasably engageable with the second member, the members being relatively movable to distract and/or compress the vertebral tissue.

17. A surgical system as recited in claim 16, wherein the flange of the first sleeve and the flange of the second sleeve each include spaced apart flexible flanges that are configured to snap fit into engagement with one of the implant supports.

18. A surgical system as recited in claim 16, wherein the surgical instrument includes a compressor/distractor having a ratchet to prevent movement of the second member relative to the first member in a first direction and/or a second direction.

19. A surgical system as recited in claim 16, wherein the surgical instrument includes a first stop engageable with the first implant support to resist and/or prevent rotation of the first implant support and a second stop engageable with the second implant support to resist and/or prevent rotation of the second implant support.

20. A surgical system as recited in claim 16, further comprising a tissue dilator positionable between the implant supports.

\* \* \* \* \*